United States Patent [19]
Crawford et al.

[11] Patent Number: 4,782,078
[45] Date of Patent: Nov. 1, 1988

[54] HALOPHOR BIOCIDAL COMPOSITIONS

[75] Inventors: Roger A. Crawford, Wadsworth; Robert H. Juda, Akron, both of Ohio; Paritosh M. Chakrabarti, Pittsburgh, Pa.

[73] Assignee: PPG Industries, Inc., Pittsburgh, Pa.

[21] Appl. No.: 819,453

[22] Filed: Jan. 16, 1986

[51] Int. Cl.$^4$ ............................................. A01N 43/36
[52] U.S. Cl. ..................................... 514/424; 548/543
[58] Field of Search ........................................... 514/424

[56] References Cited

U.S. PATENT DOCUMENTS 3,907,720  9/1975  Field et al. ............................. 521/54
4,526,751  7/1985  Gartner ........................... 424/150 X

OTHER PUBLICATIONS

Daniels et al. J.A.C.S., 28, pp. 573 and 574.

Primary Examiner—Richard L. Raymond
Assistant Examiner—D. B. Springer
Attorney, Agent, or Firm—Irwin M. Stein

[57] ABSTRACT

Halophor biocidal compositions, e.g., bromophors, comprising a complex of N-alkyl substituted-2-pyrrolidone, e.g., N-methyl pyrrolidone, halide ion, e.g., sodium bromide, and halogen, e.g., bromine, are described.

7 Claims, No Drawings

HALOPHOR BIOCIDAL COMPOSITIONS

DESCRIPTION OF THE INVENTION

The present invention relates to solid biocidal bromine- and iodine-containing compositions and, in particular, relates to complexes of bromine and/or iodine with N-alkyl substituted-2-pyrollidones.

The halogens, i.e., chlorine, bromine and iodine, are recognized as excellent biocidal materials and are used extensively, particularly in the food processing and handling industries, to prevent bacteriological contamination of foodstuffs. Halogen sanitizers are also used in controlling potentially harmful organisms in potable water, swimming pools, hospitals, and wherever harmful organisms can present a contamination problem.

Numerous proposals have been made to provide biocidal compositions which involve the complexing of halogen, e.g., bromine and iodine, with various compounds which have the property of liberating the halogen under conditions of use. These compositions are generally referred to in the art as halophors, e.g., iodophors and bromophors, and their disinfectant and germicidal activity is derived essentially from the free halogen which the compositions liberate.

Complexes of iodine with cross-linked N-vinyl lactams, e.g., N-vinyl-2-pyrrolidone or N-alkyl-N-vinylamide, polymers are described in U.S. Pat. No. 3,907,720. European Patent Application No. 107,277 describes an antimicrobial film consisting essentially of 30 to 80 weight percent vinyl acetate and 20 to 70 weight percent N-vinyl pyrrolidone copolymer combined with iodine and/or bromine. Pyrrolidone-2 has been reacted with bromine in chloroform to produce the addition product, pyrollidone-2 hydrotribromide, having the empirical formula, $[(C_4H_7NO)_3 \cdot HBr \cdot Br_2]$. N-methylpyrrolidone-2 has been reacted with hydrogen bromide and bromine to form a complex having the empirical formula $[(C_5H_{10}NO)_2 \cdot HBr \cdot Br_2]$. See, "Lactam Complexes of Bromine-Hydrogen Bromide" by W. E. Daniels et al, J. Org. Chem., Vol. 28, pp. 573–574 (Feburary, 1963).

The present invention provides a composition comprising a complex of bromine and/or iodine, an N-alkyl substituted-2-pyrrolidone organic carrier, and alkali or alkaline earth metal bromide or iodide ion. The resulting composition, i.e., the halophor, is easily handled and has exceptional stability. More particularly, the organic carrier is represented by the following graphic formula:

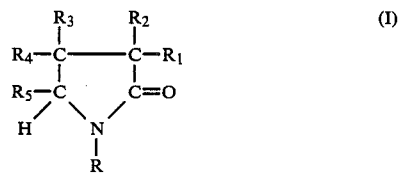

wherein R is a $C_1$–$C_4$ alkyl, and $R_1$, $R_2$, $R_3$, $R_4$ and $R_5$ are each selected from the group consisting of hydrogen and C1–C2 alkyl. The iodide or bromide used to prepare the complex is typically an alkali metal or alkaline earth metal iodide or bromide, e.g., sodium or lithium iodide or bromide, or calcium or magnesium bromide or iodide.

DETAILED DESCRIPTION OF THE INVENTION

N-alkyl substituted-2-pyrrolidones that may be used as the organic carrier for the halogen, e.g., bromine, are those represented by the above graphic formula I. More particularly, those pyrrolidones wherein R is methyl and $R_1$–$R_5$ are hydrogen or methyl are preferred. Examples of the aforedescribed pyrrolidones are N-methyl pyrrolidone, N-methyl-3-methyl pyrrolidone, N-methyl-3-ethyl pyrrolidone, N-methyl 4-methyl pyrrolidone, N-methyl-5-ethyl pyrrolidone, N-methyl-3,4-dimethyl pyrrolidone, N-methyl-3,5-dimethyl pyrrolidone, N-methyl-4,4-dimethyl pyrrolidone, N-methyl-3,3,5-trimethyl pyrrolidone, N-ethyl pyrrolidone. N-propyl pyrrolidone, N-ethyl-3-methyl pyrrolidone, and N-butyl pyrrolidone.

N-methyl pyrrolidone is a commercially available product. It may be prepared by the reaction of gamma-butyrolactone and methylamine. 2-pyrrolidones may be prepared by the reaction of butyrolactone and ammonia. The 2-pyrrolidones may be alkylated by first forming the alkali metal salt thereof and then reacting it with an alkyl halide. The N-($C_1$–$C_4$) alkyl-2-pyrrolidones may be prepared by the aforesaid alkylation method or by reaction of gamma-butyrolactone with the corresponding alkylamine in the manner in which N-methyl pyrrolidone is prepared.

The added bromide or iodide (halide) ion used in the preparation of the halophor contemplated herein is provided usually by the bromides or iodides of the alkali metals, sodium, lithium or potassium, or the bromides or iodides of the alkaline earth metals calcium and magnesium. Preferably, the aforesaid alkali metal halide is soluble or at least partially soluble in the organic carrier, i.e., the N-alkyl substituted pyrrolidone-2 or the alkyl derivatives thereof. Lithium or sodium bromide are preferred. Sodium bromide is economically preferred. The halide may be represented by the formula, MX, wherein M is the alkali metal, sodium, lithium or potassium and X is iodine or bromine, e.g., MBr or MI.

The amount of added halide used with the N-alkyl substituted-2-pyrrolidone carrier can vary. In general, the mole ratio of added halide ion to elemental halogen in the halophor composition, e.g., bromide:bromine ($Br_2$), may vary from 1:1 to 1:12, more usually from 1:1 to 1:3. Preferably, the mole ratio is about 1:2. Depending on the halide (bromide or iodide) ion and halogen (bromine or iodine) used, the halophor (bromophor or iodophor) may contain one or more of the following halide or interhalide species: $Br_3^-$ and $Br_2$ multiples thereof, e.g., $Br_5^-$, $Br_7^-$, $Br_9^-$ etc; $Br_2I^-$ and $Br_2$ multiples thereof, e.g., $Br_4I^-$, $Br_6I^-$; $BrI_2^-$ and $Br_2$ or $I_2$ multiples thereof, e.g., $Br_3I_2^-$, $Br_5I_2^-$, $BrI_4^-$, and $BrI_6^-$ etc; and $I_3^-$, and $I_2$ multiples thereof, e.g., $I_5^-$, $I_7^-$, etc.

The amount of halogen, e.g., bromine, complexed with the pyrrolidone-added halide mixture may vary widely. Usually the amount of halogen present in the halophor as available elemental halogen, e.g., $Br_2$ or $I_2$, will vary from about 10 to about 50, e.g., 25 to 40 weight percent.

In accordance with a preferred embodiment of the present invention, the added halide, i.e., alkali metal halide, is first admixed with, or preferably dissolved in, the pyrrolidone organic carrier and subsequently halogen, i.e., bromine and/or iodine, introduced into the admixture or solution. While not wishing to be bound by any theory, it is believed that the halogen added to the pyrrolidone carrier—added halide mixture reacts predominantly with the alkali metal halide to form polyhalo species rather than reacting irreversibly with the pyrrolidone carrier, thereby providing a product which yields significant quantities of available halogen, e.g., bromine, for those applications, e.g., biocidal applications, requiring same. In a preferred embodiment, the pyrrolidone carrier and halide, e.g., lithium or sodium bromide, are substantially free of water. Most preferably, the system is anhydrous, which, it is believed, leads to enhanced stability of the halophor prepared in accordance with the present process.

Halophors described herein can be readily produced by combining the pyrrolidone, alkali metal halide, and bromine (and/or iodine) under suitable complexing conditions. For bromophors, it is preferred that liquid bromine be combined with a mixture, e.g., solution, of the pyrrolidone carrier and alkali metal bromide, e.g., sodium or lithium bromide. The reaction between liquid bromine and the pyrrolidone—added halide liquid mixture is generally highly exothermic and hence the reaction mixture should be vigorously stirred and cooled as needed as the bromine is added slowly. It is generally advisable to maintain the temperature of the reaction mixture from about 25° C. to about 55° C. for best results. The reaction between iodine and the pyrrolidone carrier-added halide liquid mixture is generally less exothermic than when bromine is used; however, the same precautions and temperatures may be used to prepare the iodophors as are used to prepare the bromophors. Temporary temperature excursions outside the aforedescribed range will yield satisfactory results as long as temperatures at which the halogen reacts irreversibly with the pyrrolidone carrier are avoided for extended periods of time.

The halophors may also be prepared in a suitable organic solvent. The solvent should be capable of dispersing and preferably dissolving the alkali metal halide; it should be sufficiently volatile so as to be readily removed from the halophor; and, it should be inert so as not to react significantly with the halogen, e.g., bromine, used to prepare the halophor, i.e., it should be substantially chemically inert with respect to the halogen. Of particular utility as a suitable solvent is methanol.

Stabilizers, such as acids that are stable under the conditions of use, may be added to the halophor. Some acids that have been suggested for use as stabilizers for halophors, e.g., bromophors, are hydrochloric acid, hydrobromic acid, phosphoric acid, and acetic acid.

The compositions of the present invention are more particularly described in the following examples which are intended as illustrative only since numerous modifications and variations therein will be apparent to those skilled in the art.

While the present invention has been illustrated by the preparation of bromophor compositions using N-methyl pyrrolidone, similar results are expected using bromophors prepared with other N-alkyl substituted-2-pyrrolidones and alkyl substituted derivatives thereof.

EXAMPLE 1

An externally cooled reaction flask was charged with 84.0 grams (0.85 mole) of N-methyl pyrrolidone and 16.0 grams (0.18 mole) of lithium bromide. The contents of the flask were mixed at room temperature, i.e., about 18° C. Thereafter, 61.3 grams (0.38 mole, 19.8 milliliters) of bromine ($Br_2$) were added slowly with stirring over thirty minutes to the reaction flask. The temperature of the contents of the reaction flask increased during addition of the bromine to between 41° C. and 46° C. The reaction mixture was maintained in that temperature range while cooling with the exception of one cooling excursion to 37° C. After all of the bromine had been added, the temperature of the reaction mixture continued to rise slowly. Cooling was continued until the temperature dropped to 44° C. at which point the reaction mixture temperature decreased slowly. The product was a crystalline solid at room temperature. This product was stored in a glass bottle at 30° C. for 16 weeks after which the test was terminated. Periodically a sample was removed from the bottle and tested by thiosulfate titration for the amount of available bromine remaining in the stored composition. Results are tabulated in Table I. The bromophor composition comprised 52.1 weight percent of N-methyl pyrrolidone, 9.9 weight percent lithium bromide and 38.0 weight percent of added bromine.

TABLE I

| Time, Wks. | % Available Bromine | Time, Wks. | % Available Bromine | Time, Wks. | % Available Bromine |
|---|---|---|---|---|---|
| Start | 28.7 | 5 | 29.0 | 11 | 28.8 |
| 3 Days | 28.3 | 6 | 28.9 | 12 | 28.0 |
| 1 | 28.2 | 7 | 28.8 | 13 | 29.6 |
| 2 | 29.0 | 8 | 29.4 | 14 | 27.1 |
| 3 | 29.1 | 9 | 28.8 | 15 | 28.6 |
| 4 | 28.8 | 10 | 29.8 | 16 | 28.6 |

The data of Table I show that the bromophor composition of the Example 1 remains stable over 16 weeks—the amount of available bromine at that time being substantially the same as the amount of bromine available when the composition was made.

EXAMPLE 2

The procedure of Example 1 was followed except that 72.6 grams (0.73 mole) of N-methyl pyrrolidone and 27.4 grams (0.18 mole) sodium iodide were used. The bromine was added over a period of 30 minutes with the reaction mixture during bromine addition requiring cooling. The reaction mixture was cooled for 15 minutes and then placed in a glass bottle for storage at 30° C. Results of samples removed periodically over 16 weeks and tested for available halogen (bromine) are tabulated in Table II. The halophor was 45.0 weight percent N-methyl pyrrolidone, 17.0 weight percent halide, reported as sodium iodide, and 38.0 weight percent halogen, reported as bromine ($Br_2$).

TABLE II

| Time, Wks. | % Available Bromine* | Time, Wks. | % Available Bromine* | Time, Wks. | % Available Bromine* |
|---|---|---|---|---|---|
| Start | 35.1 | 4 | 25.1 | 9 | 24.3 |
| 3 Days | 30.2 | 5 | 24.0 | 10 | 27.8 |
| 1 | 28.7 | 6 | 25.4 | 11 | 27.8 |
| 2 | 27.8 | 7 | 25.2 | 12 | 28.0 |
| 3 | 26.0 | 8 | 28.0 | 16 | 28.3 |

*Calculated as available bromine.

The data of Table II show that the halophor composition of Example 2 remains relatively stable over 16 weeks after an initial loss of available bromine.

EXAMPLE 3

The procedure of Example 1 was followed except that 103.2 grams (1.04 mole) of N-methylpyrrolidone, 46.8 grams (0.31 mole) of sodium iodide, and 50.0 grams (0.31 mole, 16.1 milliliters) of bromine ($Br_2$) were used. The N-methyl pyrrolidone and sodium iodide were mixed and heated to 55° C. The mixture was cooled to 40° C. and the bromine slowly added over 20 minutes to the cooled mixture with stirring and external cooling. The reaction mixture temperature varied in the range of 41° C–47° C. The final product was a clear reddish brown liquid. It was cooled to 30° C. and placed in a glass bottle and stored at 30° C. Results of samples removed periodically and tested for available halogen (bromine) are tabulated in Table III. The halophor was 51.6 weight percent N-methyl pyrrolidone, 23.4 weight percent halide, reported as sodium iodide, and 25.0 weight percent halogen, reported as bromine ($Br_2$).

TABLE III

| Time, Wks. | % Available Bromine* | Time, Wks. | % Available Bromine* | Time, Wks. | % Available Bromine* |
|---|---|---|---|---|---|
| Start | 25.2 | 1 | 24.5 | 4 | 24.2 |
| 3 Days | 24.8 | 2 | 23.9 | 6 | 23.7 |
|  |  |  |  | 9 | 23.9 |

*Calculated as available bromine.

Although the present invention has been described with reference to specific details of certain embodiments thereof, it is not intended that such details should be regarded as limitations upon the scope of the invention except as and to the extent that they are included in the accompanying claims.

We claim:

1. A halophor consisting essentially of a substantially water-free complex of (a) elemental halogen selected from the group consisting of bromine and iodine, (b) added halide represented by the formula, MX, wherein M is an alkali metal selected from sodium, lithium and potassium, or alkaline earth metal selected from calcium and magnesium, and X is bromine or iodine, and (c) N-alkyl substituted-2-pyrrolidone represented by the graphic formula:

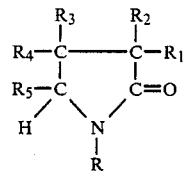

wherein R is a $C_1$–$C_4$ alkyl, and $R_1$, $R_2$, $R_3$, $R_4$ and $R_5$ are each selected from the group consisting of hydrogen and $C_1$–$C_2$ alkyl, the mole ratio of added halide to halogen being from about 1:2 to 1:12, and the amount of available elemental halogen in the halophor complex being between about 10 and about 50 weight percent.

2. The halophor of claim 1 wherein the mole ratio of added halide to halogen is from about 1:1 to 1:3.

3. The halophor of claim 1 wherein the amount of available elemental halogen is from about 25 to 40 weight percent.

4. The halophor of claim 1 wherein the halogen is bromine, the added halide is sodium bromide, lithium bromide or potassium bromide, and the N-alkyl substituted-2-pyrrolidone is N-methyl pyrrolidone.

5. A bromophor comprising a substantially water-free complex of (a) bromine, (b) alkali metal halide selected from the group consisting of sodium bromide, lithium bromide or potassium bromide, and (c) N-methyl pyrrolidone, the mole ratio of alkali metal halide to bromine being from about 1:1 to 1:3, and the amount of available elemental bromine in the bromophor complex being between about 10 and about 50 weight percent.

6. The bromophor of claim 5 wherein the amount of available elemental bromine in the bromophor complex is between about 25 and 40 weight percent.

7. The bromophor of claim 5 wherein the alkali metal halide is lithium iodide, sodium iodide or potassium iodide.

* * * * *